United States Patent
Schmitt et al.

(10) Patent No.: US 8,129,563 B2
(45) Date of Patent: Mar. 6, 2012

(54) METHOD FOR SYNTHESIZING ALLYL METHACRYLATE

(75) Inventors: Bardo Schmitt, Mainz-Kastel (DE); Guido Protzmann, Bensheim (DE); Thorben Schuetz, Seeheim-Jugenheim (DE); Harald Trauthwein, Buerstadt (DE); Reinhold Martin, Bad Koenig (DE); Joachim Knebel, Alsbach-Haehnlein (DE); Ingo Sander, Min Hang District (CN); Klaus Gottmann, Heppenheim (DE); Thomas Kehr, Muehltal (DE); Dieter Bathen, Duisburg (DE); Christian Maul, Neustadt a.d.W. (DE)

(73) Assignee: Evonik Roehm GmbH, Darmstadt (DE)

( * ) Notice: Subject to any disclaimer, the term of this patent is extended or adjusted under 35 U.S.C. 154(b) by 130 days.

(21) Appl. No.: 12/667,604

(22) PCT Filed: May 8, 2008

(86) PCT No.: PCT/EP2008/055669
§ 371 (c)(1),
(2), (4) Date: Jan. 4, 2010

(87) PCT Pub. No.: WO2009/003746
PCT Pub. Date: Jan. 8, 2009

(65) Prior Publication Data
US 2010/0185009 A1    Jul. 22, 2010

(30) Foreign Application Priority Data
Jul. 5, 2007  (DE) ................. 10 2007 031 468

(51) Int. Cl.
*C07C 67/02* (2006.01)
*C07C 69/52* (2006.01)
(52) U.S. Cl. ........................................ 560/217; 560/225
(58) Field of Classification Search ....................... None
See application file for complete search history.

(56) References Cited

U.S. PATENT DOCUMENTS

| 4,202,990 | A | * | 5/1980 | Murakami et al. ............. 560/217 |
| 5,856,611 | A | * | 1/1999 | Schlaefer et al. ............. 585/520 |
| 6,639,099 | B1 | | 10/2003 | Knebel et al. | |
| 2002/0123643 | A1 | * | 9/2002 | Paul ............................. 560/217 |

FOREIGN PATENT DOCUMENTS

EP    1 078 913    2/2001

OTHER PUBLICATIONS

U.S. Appl. No. 12/667,822, filed Jan. 5, 2010, Knebel, et al.
U.S. Appl. No. 12/667,538, filed Jan. 4, 2010, Knebel, et al.
U.S. Appl. No. 12/667,599, filed Jan. 4, 2010, Protzmann, et al.

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

The present invention relates to a process for preparing allyl methacrylate, comprising the reaction of allyl alcohol with an ester of methacrylic acid, wherein the reaction is catalyzed by zirconium acetylacetonate. The process according to the invention enables particularly favorable preparation of allyl methacrylate with a very high purity.

26 Claims, No Drawings

METHOD FOR SYNTHESIZING ALLYL METHACRYLATE

The present invention relates to processes for preparing allyl methacrylate.

Allyl methacrylate serves, inter alia, as an intermediate for preparing silyl-containing methacrylates. Accordingly, various methods of obtaining this compound are known. These include especially processes in which allyl alcohol is reacted with methacrylates, for example methyl methacrylate or ethyl methacrylate. To improve the yield and the selectivity of the reaction, different catalysts can be used.

For example, acids or bases can be used to catalyse the transesterification. Such reactions are detailed, for example, in CN 1410412 or DE 34 23 441. When these catalysts are used, however, side reactions have to be expected, for example Michael addition, which reduces both the purity of the allyl methacrylate desired and the yield.

According to the publication JP 11222461, the transesterification of methyl methacrylate with allyl alcohol can be catalysed by titanium alkoxides. In this case, nitrogen-containing polymerization inhibitors in particular are used, which, though, are undesired in the allyl methacrylate.

Moreover, publication JP-01-258642 describes the reaction of methyl methacrylate with allyl alcohol in the presence of titanium alkoxides. In this case, oxygen-containing polymerization inhibitors are used.

Furthermore, publication DE 28 05 702 describes the preparation of esters of unsaturated carboxylic acids. To catalyse the reactions described, it is possible in particular to use compounds which contain zirconium and/or calcium. The particularly suitable catalysts include especially zirconium acetylacetonate. However, the preparation of allyl methacrylate is not described explicitly. The reactions lead to high yields of approx. 98% based on the alcohol used. However, it is evident from this that the product contains considerable amounts of by-products.

The preparation of silyl-containing methacrylates from allyl alcohol requires a very high purity of the reactants, since impurities, for example allyl alcohol and water, can deactivate the Pt catalyst used for the synthesis of the silane methacrylate. Nitrogen-containing secondary components are disruptive in the same way. Allyl methacrylate, which is sold commercially as a reactant for these purposes, must therefore not contain more than 200 ppm of allyl alcohol, a minimum content of allyl alcohol being desirable. In order to satisfy these requirements, the products obtained according to the prior art must be purified in a complicated manner.

In view of the prior art, it was an object of the present invention to provide a process for preparing allyl methacrylate, in which the product is obtained with a very high purity. In particular, the allyl methacrylate obtained should contain only very small amounts of allyl alcohol and/or water.

It was a further object of the invention to provide a process in which allyl methacrylate can be obtained very selectively.

Furthermore, it was an object of the present invention to provide processes for preparing allyl methacrylate which can be performed simply and inexpensively. At the same time, the product should be obtained in maximum yields and, viewed overall, with minimum energy consumption. Furthermore, the reaction should be performable especially without nitrogen-containing polymerization inhibitors.

These objects and further objects which are not stated explicitly but which are immediately derivable or discernible from the connections discussed herein by way of introduction are achieved by processes having all the features of claim 1. Appropriate modifications to the processes according to the invention are protected in the dependent claims referring back to claim 1.

The present invention accordingly provides a process for preparing allyl methacrylate, comprising the reaction of allyl alcohol with an ester of methacrylic acid, wherein the reaction is catalysed by zirconium acetylacetonate.

As a result, it is possible in an unforeseeable manner to provide a process for preparing allyl methacrylate in which the product is obtained with a very high purity. Surprisingly, the product obtained contains only very small amounts of allyl alcohol and/or water.

Furthermore, the process according to the invention enables particularly selective preparation of allyl methacrylate.

Moreover, the process according to the invention can be performed simply and inexpensively, while the product can be obtained in high yields and, viewed overall, with low energy consumption. Furthermore, the reaction can be performed especially without nitrogen-containing polymerization inhibitors.

According to the invention, allyl methacrylate is prepared. Allyl methacrylate (propenyl 2-methylpropenoate) has been known for some time and has the CAS number 96-05-9.

To prepare allyl methacrylate, in accordance with the invention, allyl alcohol (2-propen-1-ol) is used, which is obtainable commercially, for example, from Lyondell. The CAS number of allyl alcohol is 107-18-6.

According to the present invention, allyl alcohol is reacted with an ester of methacrylic acid. Particularly suitable methacrylates are formed especially from alcohols having 1 to 4 carbon atoms. These include especially methanol, ethanol, n-propanol, isopropanol, n-butanol and tert-butanol. Particular preference is given to using especially ethyl methacrylate or methyl methacrylate, very particular preference being given to methyl methacrylate.

The weight ratio of allyl alcohol to the ester of methacrylic acid is preferably in the range of 1:1.5 to 1:10, more preferably 1:2.5 to 1:5 and most preferably in the range of 1:3 to 1:4. Too small an ester excess can reduce the reaction rate; too great an ester excess is economically unviable, since it reduces the utilizable tank volume.

According to the invention, zirconium acetylacetonate is used to catalyse the present transesterification. The CAS number of zirconium acetylacetonate is 17501-44-9. The preparation of zirconium acetylacetonate from acetylacetone (pentane-2,4-dione) and zirconium compounds is described, for example, in Houben-Weyl, Methoden der organischen Chemie [Methods of Organic Chemistry], 4th Edition, Vol. VI/2, 1963, pages 53-55 and 58 to 61, and also in A. E. Martell, M. Calvin, "Die Chemie der Metallchelatverbindungen" [The chemistry of the metal-chelate compounds] (1958). Advantageously, it is possible to use 0.2 to 5 mmol, more preferably 0.5 to 2 mmol, of zirconium acetylacetonate per mole of allyl alcohol. The catalyst can also be prepared in situ, in which case the starting materials can be added before or during the transesterification of the reaction mixture.

The reaction can be effected at elevated or reduced pressure. In a particularly appropriate modification of the present invention, the transesterification can be performed at a pressure in the range of 200 to 2000 mbar, more preferably in the range of 500 to 1300 mbar.

The reaction temperature may, especially depending on the pressure, likewise be within a wide range. In a preferred embodiment of the present invention, the reaction is effected preferably at a temperature in the range of 80° C. to 120° C., more preferably 95° C. to 115° C.

Surprisingly, particular advantages can be achieved if the temperature at which the reaction is effected is increased in the course of the reaction. In this preferred modification of the process according to the invention, the temperature at the start of the reaction, especially up to a conversion of 80%, preferably up to a conversion of 70%, based on the weight of the allyl alcohol used, may preferably be in the range of 90° C. to 100° C., and, towards the end of the reaction, especially after a conversion of 80%, preferably after a conversion of 90%, based on the weight of the allyl alcohol used, may be in the range of 105° C. to 115° C.

The transesterification can be performed either continuously or batchwise. It is also possible not to initially charge a portion of the methacrylic ester used for the transesterification before the start of the reaction but rather to meter it in actually during the reaction. The process according to the invention can be performed in bulk, i.e. without use of a further solvent. If desired, it is also possible to use an inert solvent. To this end, it is possible to use, among other solvents, petroleum, benzene, toluene, n-hexane, cyclohexane and methyl isobutyl ketone (MIBK), methyl ethyl ketone (MEK).

In a particularly appropriate variant of the inventive transesterification, all components, for example the allyl alcohol, the methacrylic ester and the catalyst, are mixed, and this reaction mixture is then heated to boiling. This heating first removes water which may be present in the alcohol in an azeotrope with the ester of methacrylic acid. Subsequently, the alcohol released, for example methanol or ethanol, can be removed from the reaction mixture by distillation, possibly in an azeotrope with methyl methacrylate or ethyl methacrylate.

In a particular modification of the present reaction, the water content in the allyl methacrylate is preferably at most 0.1%, more preferably at most 0.02%, based on the weight of the composition.

The reaction times are dependent, among other factors, on the parameters selected, for example pressure and temperature. However, they are generally in the range of 1 to 24 hours, preferably of 3 to 12 hours and more preferably 6 to 9 hours. In continuous processes, the residence times are generally in the range of 0.5 to 24 hours, preferably of 1 to 12 hours and most preferably to 3 hours. Further information with regard to the reaction times can be taken by the person skilled in the art from the examples adduced.

The reaction can preferably take place with stirring, in which case the stirrer speed may more preferably be in the range of 50 to 2000 rpm, most preferably in the range of 100 to 500 rpm.

The pH may be within a wide range. Appropriately, the reaction can be performed at a pH in the range of 5 to 9, preferably 6 to 8.

In order to prevent an undesired polymerization of the methacrylates, polymerization inhibitors can be used in the reaction. These compounds, for example hydroquinones, hydroquinone ethers such as hydroquinone monomethyl ether or di-tert-butylpyrocatechol, phenolthiazine, p-phenylenediamine, methylene blue or sterically hindered phenols, are widely known in the technical field. These compounds can be used individually or in the form of mixtures and are generally commercially available. The stabilizers usually act as free-radical scavengers for free radicals occurring in the course of polymerization. For further details, reference is made to the relevant technical literature, especially to Römpp-Lexikon Chemie; Editors: J. Falbe, M. Regitz; Stuttgart, New York; 10th Edition (1996); under "antioxidants" and the references cited at this point.

Particularly appropriate polymerization inhibitors include those which do not contain nitrogen. Preference is given to using especially phenols as the polymerization inhibitor. Particularly surprising advantages can be achieved in the case of use of mixtures which comprise hydroquinone and hydroquinone monomethyl ether. Based on the weight of the overall reaction mixture, the proportion of the inhibitors, individually or as a mixture, may generally be 0.01-0.5% (wt/wt). At the same time, it is appropriate to supply not only the reaction vessel but also the column and optionally the condenser surfaces with inhibitors, which can, for example, be metered into the column reflux.

For inhibition, it is additionally possible to use oxygen. In this case, it can be used, for example, in the form of air, in which case the amounts are advantageously metered in such that the content in the gas phase above the reaction mixture remains below the explosion limit. Particular preference is given here to amounts of air in the range of 0.05 to 0.5 l per hour and mole of allyl alcohol. In batch processes, this amount can be based on the originally used amount of allyl alcohol. In continuous processes, this amount can be based on the amount of allyl alcohol supplied. It is equally possible to use inert gas-oxygen mixtures, for example nitrogen-oxygen, argon-oxygen or carbon dioxide-oxygen mixtures.

In a particular embodiment of the present invention, a combination of oxygen with at least one phenol, preferably hydroquinone and/or hydroquinone monomethyl ether, can be used for inhibition.

In accordance with an appropriate embodiment of the present invention, the alcohol released from the methacrylate used, for example methanol and/or ethanol, can be removed by distillation. In this case, it is advantageously possible to remove, for example, a mixture which comprises methyl methacrylate and methanol. Surprisingly, a portion of the mixture removed can advantageously be recycled into the next batch. In this modification, the recyclable portion of the mixture removed can be obtained towards the end of the reaction, especially after a conversion of 80%, preferably after a conversion of 90%, of the allyl alcohol used. For example, the portion of the mixture recycled at the start of the next batch may be in the range of 40 to 60%, based on the total weight of methacrylic ester to be transesterified.

In batch processes, excess reactant, especially the unconverted ester of methacrylic acid, can be removed by distillation towards the end of the reaction. This too can be used again in the next batch without further purification.

The methanol- or ethanol-rich distillate obtained at the start of the reaction can likewise be recycled, for example by incorporation into a plant operated in an integrated system for preparing the methacrylate ester to be transesterified.

A suitable plant for performing the present transesterification may, for example, comprise a stirred tank reactor with stirrer, steam boiler, distillation column and condenser. Such plants are known per se and are described, for example, in Ullmann's Encyclopedia of Industrial Chemistry (6th Edition), Verlag Wiley-VCH, Weinheim 2003, Volume 10, page 647. The size of the plant depends on the amount of allyl methacrylate to be prepared, and the present process can be performed either on the laboratory scale or on the industrial scale. In a particular aspect, the stirred tank reactor may accordingly have a tank volume in the range of 1 $m^3$ to 20 $m^3$, preferably 3 $m^3$ to 10 $m^3$. The stirrer of the reactor tank may be configured especially in the form of an anchor stirrer, impeller, paddle stirrer or Inter-MIG stirrer.

The task of the distillation column is to ensure that a methanol- or ethanol-rich azeotrope is removed in order to minimize the losses of reactant ester which is inevitably also discharged.

The distillation column may have one, two or more separating stages. The number of separating stages refers to the number of trays in a tray column or the number of theoretical plates in the case of a column with structured packing or a column with random packing. Examples of a multistage distillation column with trays include those such as bubble-cap trays, sieve trays, tunnel-cap trays, valve trays, slot trays, slotted sieve trays, bubble-cap sieve trays, nozzle trays, centrifugal trays, and examples of a multistage distillation column with random packings include those such as Raschig rings, Lessing rings, Pall rings, Berl saddles, Intalox saddles, and examples of a multistage distillation column with structured packing include those such as the Mellapak (Sulzer), Rombopak (Kühni), Montz-Pak (Montz) type. As a result of the conversion-dependent adjustment of the reflux ratio, it is possible, for example, in the case of use of methyl methacrylate, to set a methanol content in the distillate which is above 60% over wide ranges of the conversion.

The suitable condensers which may be present in the plant for performing the present transesterification include plate heat exchangers and tube bundle heat exchangers.

After the reaction has ended, the allyl methacrylate obtained in many cases already satisfies the high requirements detailed above, such that further purification is in many cases unnecessary. To further enhance the quality and especially to remove the catalyst, the mixture obtained can be purified by known processes. Owing to the polymerization tendency of the monomer, advisable distillation processes are those in which the thermal stress on the substance to be distilled is minimized. Very suitable apparatus is that in which the monomer is evaporated continuously from a thin layer, such as falling-film evaporators and evaporators with a rotating wiper system. It is also possible to use short-path evaporators. Such apparatus is known (Ullmann's Encyclopedia of Industrial chemistry (6th Edition), Verlag Wiley-VCH, Weinheim 2003, Volume 36, page 505). For example, it is possible to perform a distillation in which a continuous evaporator with a rotating wiper system and attached column can be used.

This distillation can be performed, for example, at a pressure in the range of 40 to 60 mbar and an evaporator temperature of 110° C. to 130° C.

It is surprisingly possible through the inventive measures to provide a process in which allyl methacrylate can be obtained which contains preferably less than 0.04%, more preferably less than 0.02% and most preferably less than 0.01% allyl alcohol, based on the weight of the composition.

The present invention will be illustrated hereinafter with reference to examples and comparative examples, without any intention that this should impose a restriction.

COMPARATIVE EXAMPLE 1

In a 7 $m^3$ stirred tank reactor with stirrer, steam boiler, distillation column and condenser, 850 kg of allyl alcohol, 4800 kg of methyl methacrylate (MMA), 0.68 kg of phenothiazine and 0.22 kg of N,N'-diphenyl-p-phenylenediamine as inhibitors, and 34 kg of lauryl titanate as the catalyst, are combined and stirred with introduction of air. The mixture is heated to bottom temperature 95° C., and the column is initially operated with full reflux. As soon as the temperature at the top of the column falls below 70° C., the methanol-MMA mixture is drawn off at a reflux ratio of 1:1. Within 8 h, the reflux ratio is adjusted to the decreasing methanol evolution up to 4.5:1. At a bottom temperature of 115° C., the reaction has ended and excess MMA is removed under reduced pressure, while the pressure is reduced gradually down to 5 torr. When no further MMA distils off, the vacuum is broken. The tank contents consist of 1780 kg of allyl methacrylate which still contains 4000 ppm of allyl alcohol and 1700 ppm of methyl methacrylate (determined by gas chromatography).

COMPARATIVE EXAMPLE 2

In a 7 $m^3$ stirred tank reactor with stirrer, steam boiler, distillation column and condenser, 1160 kg of allyl alcohol, 4800 kg of methyl methacrylate (MMA), 1.79 kg of hydroquinone and 0.34 kg of hydroquinone monomethyl ether as inhibitors, and 34 kg of lauryl titanate as the catalyst, are combined and stirred with introduction of air. The mixture is heated to bottom temperature 95° C., and the column is initially operated with full reflux. As soon as the temperature at the top of the column falls below 70° C., the methanol-MMA mixture is drawn off at a reflux ratio of 1:1. Within 8 h, the reflux ratio is adjusted to the decreasing methanol evolution up to 4.5:1. At a bottom temperature of 115° C., the reaction has ended and excess MMA is removed under reduced pressure, while the pressure is reduced gradually down to 5 torr. When no further MMA distils off, the vacuum is broken. The tank contents consist of 2500 kg of allyl methacrylate which still contains 1200 ppm of allyl alcohol and 7400 ppm of methyl methacrylate (determined by gas chromatography).

EXAMPLE 1

In a 7 $m^3$ stirred tank reactor with stirrer, steam boiler, distillation column and condenser, 1275 kg of allyl alcohol, 4800 kg of methyl methacrylate (MMA), 1.8 kg of hydroquinone and 0.34 kg of hydroquinone monomethyl ether as inhibitors, and 7.7 kg of zirconium acetylacetonate as the catalyst, are combined and stirred with introduction of air. The mixture is heated to bottom temperature 95° C., and the column is initially operated with full reflux. As soon as the temperature at the top of the column falls below 70° C., the methanol-MMA mixture is drawn off at a reflux ratio of 1:1. Within 8 h, the reflux ratio is adjusted to the decreasing methanol evolution up to 4.5:1. At a bottom temperature of 115° C., the reaction has ended and excess MMA is removed under reduced pressure, while the pressure is reduced gradually down to 5 torr. When no further MMA distils off, the vacuum is broken. The tank contents consist of 2500 kg of allyl methacrylate which contains only 30 ppm of allyl alcohol and 4280 ppm of methyl methacrylate (determined by gas chromatography).

EXAMPLE 2

In a 7 $m^3$ stirred tank reactor with stirrer, steam boiler, distillation column and condenser, 1326 kg of allyl alcohol, 4800 kg of methyl methacrylate (MMA), 1.8 kg of hydroquinone and 0.34 kg of hydroquinone monomethyl ether as inhibitors, and 7.7 kg of zirconium acetylacetonate as the catalyst, are combined and stirred with introduction of air. The mixture is heated to bottom temperature 95° C., and the column is initially operated with full reflux. As soon as the temperature at the top of the column falls below 70° C., the methanol-MMA mixture is drawn off at a reflux ratio of 1:1. Within 8 h, the reflux ratio is adjusted to the decreasing methanol evolution up to 4.5:1. At a bottom temperature of 115° C., the reaction has ended and excess MMA is removed under reduced pressure, while the pressure is reduced gradually down to 5 torr. When no further MMA distils off, the vacuum is broken. The tank contents consist of 2740 kg of allyl methacrylate which contains only 10 ppm of allyl alcohol and 4120 ppm of methyl methacrylate (determined by gas chromatography).

EXAMPLE 3

In a 7 m$^3$ stirred tank reactor with stirrer, steam boiler, distillation column and condenser, 1340 kg of allyl alcohol, 4880 kg of methyl methacrylate (MMA), 1.8 kg of hydroquinone and 0.34 kg of hydroquinone monomethyl ether as inhibitors, and 7.7 kg of zirconium acetylacetonate as the catalyst, are combined and stirred with introduction of air. The mixture is heated to bottom temperature 95° C., and the column is initially operated with full reflux. As soon as the temperature at the top of the column falls below 70° C., the methanol-MMA mixture is drawn off at a reflux ratio of 1:1. At the same time, 700 kg of MMA are metered into the mixture within 4 h at a rate which corresponds to the amount of methanol-MMA discharged per unit time. Within 8 h, the reflux ratio is adjusted to the decreasing methanol evolution up to 4.5:1. At a bottom temperature of 117° C., the reaction has ended and excess MMA is removed under reduced pressure, while the pressure is reduced gradually down to 5 torr. When no further MMA distils off, the vacuum is broken. The tank contents consist of 2680 kg of allyl methacrylate which contains only 50 ppm of allyl alcohol and 1160 ppm of methyl methacrylate (determined by gas chromatography).

Distillative Purification of the Allyl Methacrylate 450 kg/h of crude allyl methacrylate are fed into a continuous evaporator (area 3.5 m$^2$) with rotating wiper system and attached column at pressure 50 mbar and evaporator temperature 120° C. At the top of the column, a temperature of 60° C. is established. 425 kg/h of distillate are drawn off, consisting of pure allyl methacrylate which is stabilized with 50 ppm of hydroquinone monomethyl ether for later storage. Composition (determined by gas chromatography)

a) starting from raw material from Comparative Example 2: 99.55% allyl methacrylate, 0.37% MMA, 0.033% allyl alcohol water content (determined by Karl-Fischer titration): 350 ppm
b) starting from raw material from Inventive Example 1: 99.71% allyl methacrylate, 0.22% MMA, 0.006% allyl alcohol water content (determined by Karl-Fischer titration): 110 ppm
c) starting from raw material from Inventive Example 3: 99.88% allyl methacrylate, 0.11% MMA, 0.005% allyl alcohol water content (determined by Karl-Fischer titration): 50 ppm

The invention claimed is:

1. A process for preparing allyl methacrylate, comprising the reaction of allyl alcohol with an ester of methacrylic acid, wherein the reaction is catalyzed by zirconium acetylacetonate.

2. The process according to claim 1, wherein methyl methacrylate is used as the ester of methacrylic acid.

3. The process according to claim 1, wherein the allyl methacrylate comprises less than 0.02 wt. % of allyl alcohol.

4. The process according to claim 1, wherein the weight ratio of allyl alcohol to the ester of methacrylic acid is in the range of 1:2.5 to 1:5.

5. The process according to claim 4, wherein the weight ratio of allyl alcohol to the ester of methacrylic acid is in the range of 1:3.0 to 1:4.0.

6. The process according to claim 1, wherein 0.5 to 2 mmol of zirconium acetylacetonate are used per mole of allyl alcohol.

7. The process according to claim 1, wherein the reaction is effected at a pressure in the range of 500 to 1300 mbar.

8. The process according to claim 1, wherein the reaction is effected at a temperature in the range of 80° C. to 120° C.

9. The process according to claim 1, wherein the temperature at which the reaction is effected is increased in the course of the reaction.

10. The process according to claim 8, wherein the temperature at the start of the reaction is in the range of 90° C. to 100° C. and is in the range of 105° C. to 115° C. towards the end of the reaction.

11. The process according to claim 1, wherein the reaction is effected in the presence of a polymerization inhibitor.

12. The process according to claim 11, wherein the polymerization inhibitor does not contain nitrogen.

13. The process according to claim 11, wherein a phenol is used as the polymerization inhibitor.

14. The process according to claim 11, wherein the polymerization inhibitor used is a mixture which comprises hydroquinone and hydroquinone monomethyl ether.

15. The process according to claim 1, wherein the allyl methacrylate comprises at most 0.02 wt. % water.

16. The process according to claim 1, wherein the reaction takes place with stirring.

17. The process according to claim 16, wherein the stirrer speed is in the range of 100 to 500 rpm.

18. The process according to claim 1, wherein the reaction is effected with introduction of atmospheric oxygen.

19. The process according to claim 18, wherein 0.05 to 0.5 l of air per hour and mole of allyl alcohol is introduced.

20. The process according to claim 1, wherein the reaction is effected at a pH in the range of 6 to 8.

21. The process according to claim 1, wherein the alcohol released from the ester of methacrylic acid used is removed by distillation.

22. The process according to claim 21, wherein ethanol or methanol is removed.

23. The process according to claim 21, wherein a mixture which comprises methyl methacrylate and methanol is removed.

24. The process according to claim 23, wherein a portion of the mixture removed is introduced into the next batch.

25. The process according to claim 24, wherein the recyclable portion of the mixture removed is obtained towards the end of the reaction.

26. The process according to claim 1, wherein the allyl methacrylate comprises less than 0.01 wt. % of allyl alcohol.

* * * * *